United States Patent
Rajaraman et al.

(10) Patent No.: US 8,362,124 B2
(45) Date of Patent: Jan. 29, 2013

(54) COATINGS AND PRINTING INK COMPOSITIONS CONTAINING SILYLATED POLYETHER SURFACTANTS AND ARTICLES MADE THEREFROM

(75) Inventors: Suresh K. Rajaraman, Macungie, PA (US); Eric R. Pohl, Mount Kisco, NY (US); Mark D. Leatherman, Stamford, CT (US); George A. Policello, Ossining, NY (US)

(73) Assignee: Momentive Performance Materials Inc., Albany, NY (US)

( * ) Notice: Subject to any disclaimer, the term of this patent is extended or adjusted under 35 U.S.C. 154(b) by 105 days.

(21) Appl. No.: 12/712,377

(22) Filed: Feb. 25, 2010

(65) Prior Publication Data

US 2010/0215922 A1     Aug. 26, 2010

Related U.S. Application Data

(60) Provisional application No. 61/155,328, filed on Feb. 25, 2009.

(51) Int. Cl.
    *C09D 11/10*     (2006.01)
    *C08K 5/5419*     (2006.01)

(52) U.S. Cl. ... 524/269; 524/265; 524/267; 106/287.13; 522/77; 523/160; 523/161

(58) Field of Classification Search ............ 106/287.13; 524/265, 267; 522/77
See application file for complete search history.

(56) References Cited

U.S. PATENT DOCUMENTS

| | | | |
|---|---|---|---|
| 2005/0203202 A1* | 9/2005 | Weine Ramsey | 522/71 |
| 2007/0249560 A1 | 10/2007 | Leatherman et al. | |
| 2007/0269467 A1 | 11/2007 | Leatherman et al. | |

FOREIGN PATENT DOCUMENTS

| | | |
|---|---|---|
| DE | 4320920 | 6/1994 |
| JP | 02-151873 | 6/1990 |
| JP | 03-105352 | 5/1991 |
| WO | 2008/073396 | 6/2008 |

OTHER PUBLICATIONS

US Army Corps of Engineers document EM 1110-2-3400, "Painting: New Construction and Maintenance" Chapter 4: "Coating Types and Characteristics", published Apr. 30, 1995, pp. 4-1 to 4-4.*

* cited by examiner

*Primary Examiner* — Vu A Nguyen
(74) *Attorney, Agent, or Firm* — Dominick G. Vicari; Joseph S. Ostroff

(57) ABSTRACT

The present invention relates to coating and printing ink compositions containing silylated polyether compounds comprising a hydrolysis-resistant bis-silyl hydrocarbylene group. More particularly, the silylated polyether compound comprising a bis-silyl hydrocarbylene group provides to the coating and ink compositions formulation flexibility over the entire pH range, leveling-and-flow and surface wetting, and are non-reactive with the other components of the coating and ink compositions, thereby providing long-term shelf-stability of formulated coatings and inks. These coating and ink compositions containing silylated polyether compounds do not release silicone materials and thereby provide articles treated with these coatings and ink compositions with uniform appearance and gloss.

16 Claims, No Drawings

COATINGS AND PRINTING INK COMPOSITIONS CONTAINING SILYLATED POLYETHER SURFACTANTS AND ARTICLES MADE THEREFROM

CROSS REFERENCE TO RELATED APPLICATIONS

This application claims priority to U.S. Provisional application No. 61/155,328 filed Feb. 25, 2009, which is herein incorporated by reference in its entirety.

FIELD OF THE INVENTION

The present invention relates to coating and printing ink compositions containing silylated polyether compounds comprising a hydrolysis-resistant bis-silyl hydrocarbylene group. More particularly, the silylated polyether compound comprising a bis-silyl hydrocarbylene group provides formulation flexibility over the entire pH range, leveling-and-flow and surface wetting, and are non-reactive with the other components of the coating and ink compositions, thereby providing long-term shelf-stability of formulated coatings and inks. These coating and ink compositions containing silylated polyether compounds do not release silicone materials and thereby are expected to provide articles treated with these coatings and ink compositions with uniform appearance and gloss.

BACKGROUND OF THE INVENTION

The topical application of compositions to the surfaces of both animate and inanimate objects to effect a desired change involve the processes of controlling wetting, spreading, flow, leveling, foaming, detergency, and the like. When used in aqueous solutions to improve the delivery of active ingredients to the surface being treated, trisiloxane-containing polyether compounds have been found to be useful in enabling the control of these processes to achieve the desired effect. However, the trisiloxane-containing polyether compounds may react with water or the other components in the coating and ink compositions to generate low levels of organosilicone materials. These organosilicone materials are released into the environment, interfere with the leveling and flow and generate coated objects that have non-uniformity and poor appearance, often referred to as "fish-eyes".

In recent years, there has been a move to waterborne coatings and inks in place of solvent-borne coatings from the viewpoints of resource savings and environmental pollution. For example, waterborne coatings have been investigated for primer coatings, base coatings and top coatings for automobiles. Waterborne coating and inks wet surfaces poorly, due to their higher surface energy and often have poor flow-and-leveling properties. A need for wetting and level-and-flow agents for waterborne coatings having the feature of imparting low surface energy to the coatings and inks without generating undesirable silicone materials exists. In order to meet this requirement, acryl base polymers, modified silicone oils and the like have so far been used as flow-and-leveling agents. However, satisfactory wetting and flow-and-leveling properties and elimination of coating defects are not necessarily achieved with these conventional techniques, especially in the fields requiring a high level of appearance for uses such as automobiles. So either large concentrations of organic surfactants or specialty perfluoroalkyl functionalized surfactants with very low surface tension are typically added in order to obtain a good appearance. One of the issues with using very high concentrations of organic surfactants is the adverse effect that it exerts on other properties of coatings, such as layer-to-layer adhesive properties in recoating or roughening the surfaces of the recoated films.

Conventional organic surfactants provide only an inadequate solution to the leveling problem in the case of coatings, and there is a need for new surfactants that make it possible to produce absolutely smooth coating films. Alternatively, specialty fluoro-based surfactants are facing pressures from toxicological and bioaccumulation fronts. The U.S. Environmental Protection Agency (EPA) is proposing to tighten regulation of such perfluoroalkyl materials that have the potential of breaking down into toxic perfluoroalkyl carboxylates, such as perfluorooctanoic acid (PFOA), and perfluoroalkyl sulfonates, including perfluorooctanyl sulfonate (PFOS). These substances are expected to bioaccumulate, persist in the environment, and may be considered "highly toxic". Also, studies suggest that perfluoroalkyl sulfonates and carboxylates may get released in the air when items made with certain fluoropolymers are burned in municipal waste incinerators.

Accordingly, the identification of non-fluorinated surfactants that can avoid environmental and health concerns is of interest. The present invention, which describes the utility and application of coating and ink compositions containing silylated polyether compounds, which are expected to provide improved appearance, flow, leveling and wetting benefits, while helping to avoid such potential environmental and health concerns.

SUMMARY OF THE INVENTION

The present invention provides a coating composition comprising:

(a) at least one silylated polyether compound of the general formula (1):

$$(R^1)(R^2)(R^3)SiR^4Si(R^5)(R^6)R^7(C_2H_4O)_a(C_3H_6O)_b(C_4H_8O)_cR^8 \quad (1)$$

wherein
each occurrence of $R^1$, $R^2$, $R^3$, $R^5$ and $R^6$ independently is a monovalent hydrocarbyl group of from 1 to 10 carbon atoms;
each occurrence of $R^4$ independently is a divalent hydrocarbylene group of 1 to 3 carbon atoms;
each occurrence of $R^7$ independently is a divalent organic group having the structure:

$$-CH_2-CH(R^9)(R^{10})_gO-$$

where each occurrence of $R^9$ independently is a hydrogen atom or methyl; each occurrence of $R^{10}$ independently is a divalent alkylene radical of 1 to 6 carbon atoms; and the subscript g is 0 or 1;
each occurrence of $R^8$ independently is selected from the group consisting of a hydrogen atom, a monovalent hydrocarbon group, and an acyl group of 1 to 12 carbon atoms; and
each occurrence of the subscripts a, b and c is an integer where a is 0 to 40, b is 0 to 18 and c is 0 to 18 with the proviso that $2 \leq a+b+c \leq 40$; and
(b) at least one coating resin.

The present invention further provides a printing ink composition comprising:

(a) at least one silylated polyether compound of the general formula (I):

$$(R^1)(R^2)(R^3)SiR^4Si(R^5)(R^6)R^7(C_2H_4O)_a(C_3H_6O)_b(C_4H_8O)_cR^8 \quad (1)$$

wherein each occurrence of $R^1$, $R^2$, $R^3$, $R^5$ and $R^6$ independently is a monovalent hydrocarbyl group of from 1 to 10 carbon atoms;

each occurrence of $R^4$ independently is a divalent hydrocarbylene group of 1 to 3 carbon atoms;

each occurrence of $R^7$ independently is a divalent organic group having the structure:

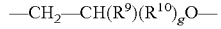
$$-CH_2-CH(R^9)(R^{10})_g O-$$

where each occurrence of $R^9$ independently is a hydrogen atom or methyl; each occurrence of $R^{10}$ independently is a divalent alkylene radical of 1 to 6 carbon atoms; and the subscript g is 0 or 1;

each occurrence of $R^8$ independently is selected from the group consisting of a hydrogen atom, a monovalent hydrocarbon group, and an acyl group of 1 to 12 carbon atoms; and each occurrence of the subscripts a, b and c is an integer where a is 0 to 40, b is 0 to 18 and c is 0 to 18 with the proviso that $2 \leq a+b+c \leq 40$; and (b) at least one printing ink resin.

The coating and printing ink compositions of the present invention are expected to exhibit enhanced appearance, wetting, leveling and flow when compared to coating and ink compositions containing organic surfactants and wetting agents, while not generating undesirable organosilicone compounds of trisiloxane-containing polyether surfactants or comprising surfactants that have the undesirable fluorine atom.

Other than in the examples or where otherwise indicated, all numbers expressing amounts of materials, reaction conditions, time durations, quantified properties of materials, and so forth, stated in the specification and claims are to be understood as being modified in all instances by the term "about".

It will also be understood that any numerical range recited herein is intended to include all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

DETAILED DESCRIPTION OF THE INVENTION

The present invention provides coating and printing ink compositions comprising at least one silylated polyether compound of the general formula (1):

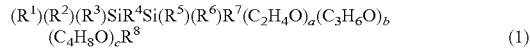
$$(R^1)(R^2)(R^3)SiR^4Si(R^5)(R^6)R^7(C_2H_4O)_a(C_3H_6O)_b(C_4H_8O)_c R^8 \quad (1)$$

wherein each occurrence of $R^1$, $R^2$, $R^3$, $R^5$ and $R^6$ independently is a monovalent hydrocarbyl group of from 1 to 10 carbon atoms;

each occurrence of $R^4$ independently is a divalent hydrocarbylene group of 1 to 3 carbon atoms;

each occurrence of $R^7$ independently is a divalent organic group having the structure:

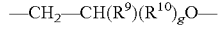
$$-CH_2-CH(R^9)(R^{10})_g O-$$

where each occurrence of $R^9$ independently is a hydrogen atom or methyl; each occurrence of $R^{10}$ independently is a divalent alkylene radical of 1 to 6 carbon atoms; and the subscript g is 0 or 1;

each occurrence of $R^8$ independently is selected from the group consisting of a hydrogen atom, a monovalent hydrocarbon group, and an acyl group of 1 to 12 carbon atoms; and each occurrence of the subscripts a, b and c is an integer where a is 0 to 40, b is 0 to 18 and c is 0 to 18 with the proviso that $2 \leq a+b+c \leq 40$.

In the context of the invention, the term "leveling" as defined herein is understood to refer to the ability of the applied coating to form a smooth film in which imperfections left by the applicator, such as a brush or roller, disappear during the drying process. The term "flow" as defined herein refers to the spreadability of the coating and to the ease with which the coating can be applied. The term "wetting" as described herein is the ability of a formulation to wet the surfaces of substrates efficiently without pinholes and defects.

As used herein, monovalent hydrocarbon groups include straight chain, branched and cyclic alkyl, alkenyl and allynyl groups, aralkyl groups and aryl groups. Specific non-limiting examples of alkyl include methyl, ethyl, propyl and isobutyl. Specific non-limiting examples of alkenyl include vinyl, propenyl, allyl and methallyl. Specific non-limiting examples of alkynyls include acetylenyl, propargyl and methylacetylenyl. Specific non-limiting examples of aralkyl include benzyl and phenethyl. Specific non-limiting example of aryl includes phenyl.

As used herein, divalent hydrocarbon groups include straight chain, branched and cyclic alkylene, alkenylene and alkynylene groups, aralkylene groups and arylene groups. Specific non-limiting examples of alkylene include methylene, ethylene, propylene and isobutylene. Specific non-limiting examples of alkenylene include ethenylene and propenylene. Specific non-limiting examples of alkynylenes include acetylenylene, propargylene and methylacetylenylene. Specific non-limiting examples of aralkylene include xylenylene. A specific non-limiting example of arylene includes phenylene.

The term "substituted" aliphatic or aromatic refers to an aliphatic or aromatic group wherein the carbon backbone may have a heteroatom located within the backbone or a heteroatom or heteroatom-containing group attached to the carbon backbone.

The term "organic group" refers to an aliphatic hydrocarbon group, aromatic hydrocarbon group, or substituted aliphatic or substituted aromatic group.

The silylated polyether compound (a) provides for a uniform coating or ink on the substrate. The preparation of the silylated polyether compounds are described in U.S. Patent Application Publication Nos. US 20070249560 A1, and US 20070269467 A1, which are both incorporated by reference herein in its entireties.

The substituents of formula (1) of silylated polyether compound (a) have been described above. Illustratively, for silylated polyether compound (a), $R^1$, $R^2$, $R^3$, $R^5$ and $R^6$ is an alkyl group of from 1 to 6 carbon atoms; $R^4$ is an alkylene group of 1 to 3 carbon atoms; $R^7$ is $-CH_2CH_2CH_2O-$ or $-CH_2CH(CH_3)CH_2O-$; $R^8$ is an hydrogen atom, an alkyl group of from 1 to 6 carbon atoms or an acetyl group; a is 3 to 10; b is 0 to 10 and c is 0 to 8. Illustratively, silylated polyether compound (a) is where $R^1$, $R^2$, $R^3$, $R^5$ and $R^6$ is methyl, ethyl, propyl, isopropyl or isobutyl; $R^4$ is ethylene; $R^7$ is $-CH_2CH_2CHO-$; $R^8$ is an hydrogen atom, methyl or an acetyl group; a is 5 to 8; b is 0 to 5; c is 0 to 2. Yet another example of the silylated polyether compound (a) is where $R^1$, $R^2$, $R^3$, $R^5$ and $R^6$ is methyl; and a is 5 to 8; b is 0 to 3 and c is 0.

Representative and non-limiting examples of the silylated polyether compound (a) are,
$(CH_3)_3SiCH_2Si(CH_3)_2CH_2CH_2O(CH_2CH_2O)_2H$,
$(CH_3)_3SiCH_2CH_2Si(CH_3)_2CH_2CH_2O(CH_2CH_2O)_3CH_3$,
$(CH_3)_3SiCH_2CH_2Si(CH_3)_2CH_2CH_2CH_2O(CH_2CH_2O)_7CH_3$,
$(CH_3)_3SiCH_2CH_2Si(CH_3)_2CH_2CH_2CH_2O(CH_2CH_2O)_{20}CH_3$,
$(CH_3)_3SiCH_2CH_2Si(CH_3)_2CH_2CH(CH_3)CH_2O(CH_2CH_2O)_4CH_3$,
$(CH_3)_3SiCH_2CH_2Si(CH_3)_2CH_2CH_2O(CH_2CH_2O)_4(CH_2CH(CH_3)O)_1CH_3$,
$(CH_3CH_2)_3SiCH_2CH_2Si(CH_2CH_3)_2CH_2CH_2O(CH_2CH_2O)_4(CH_2CH(CH_3)O)_1CH_3$,
$(CH_3CH_2CH_2)_3SiCH_2CH_2Si(CH_2CH_2CH_3)_2CH_2CH_2O(CH_2CH_2O)_4(CH_2CH(CH_3)O)_1CH_3$,
$(CH_3)_2(CH_3CH_2CH_2)SiCH_2CH_2Si(CH_3)_2CH_2CH_2O(CH_2CH_2O)_4(CH_2CH(CH_3)O)_1CH_3$,
$(CH_3)_2(C_6H_5CH_2CH_2)SiCH_2CH_2Si(CH_3)_2CH_2CH_2O(CH_2CH_2O)_7(CH_2CH(CH_3)O)_1CH_3$,
$(CH_3)_3SiCH_2CH_2Si(CH_3)_2CH_2CH_2CH_2O(CH_2CH_2O)_5(CH_2CH(CH_3)O)_2CH_3$,
$(CH_3)_3SiCH_2CH_2Si(CH_3)_2CH_2CH_2CH_2O(CH_2CH_2O)_{15}(CH_2CH(CH_3)O)_5H$,
$(CH_3)_3SiCH_2CH_2Si(CH_3)_2CH_2CH_2CH_2O(CH_2CH_2O)_2(CH_2CH(CH_3)O)_{18}CH_3$,
$(CH_3)_3SiCH_2CH_2Si(CH_3)_2CH_2CH_2CH_2O(CH_2CH_2O)_8(CH_2CH(CH_3)O)_3CH_3$,
$(CH_3)_3SiCH_2CH_2Si(CH_3)_2CH_2CH_2CH_2O(CH_2CH_2O)_4(CH_2CH(CH_2CH_3)O)_1CH_3$,
$(CH_3)_3SiCH_2CH_2Si(CH_3)_2CH_2CH_2CH_2O(CH_2CH_2O)_{10}(CH_2CH(CH_2CH_3)O)_5CH_3$,
$(CH_3)_3SiCH_2CH_2Si(CH_3)_2CH_2CH_2CH_2O(CH_2CH_2O)_{10}(CH_2CH(CH_2CH_3)O)_{10}C(=O)CH_3$,
$(CH_3)_3SiCH_2CH_2Si(CH_3)_2CH_2CH_2O(CH_2CH_2O)_4CH_2CH(CH_3)OCH_2CH(CH_2CH_3)OH$,
$(CH_3)_3SiCH_2CH_2Si(CH_3)_2CH_2CH_2O(CH_2CH_2O)_8(CH_2CH(CH_3)O)_5CH_2CH(CH_2CH_3)OH$
$(CH_3)_3SiCH_2CH_2Si(CH_3)_2CH_2CH_2CH_2O(CH_2CH_2O)_4(CH_2CH(CH_3)O)_1CH_3$,
$(CH_3)_3SiCH_2CH_2CH_2Si(CH_3)_2CH_2CH_2O(CH_2CH_2O)_4CH_3$,
$(CH_3)_3SiCH_2CH_2CH_2Si(CH_3)_2CH_2CH_2O(CH_2CH_2O)_5C(=O)CH_3$,
$(CH_3)_3SiCH_2CH_2CH_2Si(CH_3)_2CH_2CH_2O(CH_2CH_2O)_4(CH_2CH(CH_3)O)_1CH_3$,
$(CH_3CH_2)_3SiCH_2CH_2CH_2Si(CH_2CH_3)_2CH_2CH_2O(CH_2CH_2O)_4(CH_2CH(CH_3)O)_1CH_3$,
$(CH_3)_3SiCH_2CH_2CH_2Si(CH_3)_2CH_2CH_2CH_2O(CH_2CH_2O)_4(CH_2CH(CH_3)O)_1CH_3$, and mixtures thereof.

The coating and printing ink compositions of the present invention containing the silylated polyether compounds described above exhibit an enhanced resistance to hydrolysis outside a pH range ranging from 6 to 7.5, i.e. in extreme environmental conditions. An extreme environment is defined as an aqueous solution pH below 6 or above 7.5 or non-aqueous equivalents in terms of Bronsted acidity or basicity or Lewis acidity or basicity. Enhanced resistance to hydrolysis can be demonstrated by a variety of tests, but as used herein, enhanced resistance to hydrolysis means 70 mole percent or more of the hydrolysis resistant composition of the present invention remains unchanged or unreacted after a period of a twenty-four hour exposure to aqueous acidic conditions where the solution has a pH of 3 and after a period of a twenty-four hour exposure to aqueous basic conditions where the solution has a pH greater than 11. Under acidic conditions the compositions of the present invention show a survival of 70 mole percent of the original concentration or greater at a pH of 3 or less for a period of time in excess of 48 hours; specifically the compositions of the present invention show a survival of 70 mole percent or greater at a pH of 3 or less for a period of time in excess of 2 weeks; more specifically the compositions of the present invention show a survival of 70 mole percent or greater at a pH of 3 or less for a period of time in excess of 1 month; and most specifically the compositions of the present invention show a survival of 70 mole percent or greater at a pH of 3 or less for a period of time in excess of 6 months. Under basic conditions the compositions of the present invention show a survival of 70 mole percent or greater at a pH of 11 or more for a period of time in excess of 2 weeks; specifically the compositions of the present invention show a survival of 70 mole percent or greater at a pH of 11 or more for a period of time in excess of 4 weeks; more specifically the compositions of the present invention show a survival of 70 mole percent or greater at a pH of 11 or more for a period of time in excess of 6 months; and most specifically the compositions of the present invention show a survival of 70 mole percent or greater at a pH of 11 or more for a period of time in excess of 1 year.

The coating and printing ink compositions of the present invention may be utilized in a variety of forms: as liquid solutions, dispersions of solids in liquids, dispersions of liquids in liquids as the previously described emulsions, solid mixtures or solid solutions either separately or in the forms previously listed in combination one with the other.

Coatings

Typically coatings formulations will require a wetting agent or surfactant for the purpose of emulsification, compatibilization of components, leveling, flow and reduction of surface defects. Additionally, these additives may provide improvements in the cured or dry film, such as improved abrasion resistance, anti-blocking, hydrophilic, and hydrophobic properties. Coatings formulations may exist as solvent-borne coatings, waterborne coatings, high solids coatings, electro-deposition coatings, radiation-curable coatings, supercritical carrier coatings, neat coatings and powder coatings.

Paint surfaces are normally not entirely smooth but instead have a more or less structured surface referred to as waviness or else as orange peel. These surfaces may be finely structured, with a short wave, or coarsely structured, with a long wave. In the majority of cases, this waviness is unwanted and a surfactant is necessary to provide flow, leveling and wetting to achieve a surface that is in any way smooth.

The coating compositions of the present invention can be employed as: architecture coatings for both interior and exterior applications; original equipment manufacturer (OEM) product coatings or finishes for automotive, marine, aircraft, a variety of land transportation, appliances, metal furniture, machinery and equipment, coil, metal containers, insulating varnishes, pipe, packaging, overprint, release, prefinished wood, wood furniture, plastic substrates, scratch off coatings, nonstick cookware, acoustic ceiling tiles, fiber sizing and general metal; and special purpose coatings such as industrial maintenance coatings, automotive refinish, traffic paints and miscellaneous coatings such as roof, tank, deck coatings, masonry coatings, masonry water repellent and concrete cure and seal coatings, and the like.

Typical coating resins (b) include but is not limited to polyesters, alkyds, acrylics, epoxies, polyurethanes, chlorinated polyolefins, polyvinylidene chloride, urethane-polyester copolymers, styrene-butadiene, acrylic-urethane copolymers, polyvinyl chloride, epoxy esters, epoxy-aminos, epoxy-phenolic, phenolic, styrene-acrylic, epoxy acrylic, urethane-acrylic, silicone, acylic-polyesters, epoxy-polyamide, polyvinyl acetate, vinyl-acrylic, silicone, silicone-acrylic, vinyl acetate-ethylene, styrene-acrylic, asphalt, coal tar, polyolefin, polyamide, hydrocarbon, vinyl acetate-acrylic and silane systems, and mixtures copolymers and terpolymers thereof and used in an amount known and conventional in the art for the particular coating application.

Accordingly, an object of the present invention is to provide novel coating compositions comprising a silylated polyether compound capable of being utilized in, but not limited to, polyesters, acrylics, epoxies, polyurethanes, urethane-polyester copolymers, acrylic-urethane copolymers, epoxy esters, epoxy-aminos, styrene-acrylic, epoxy acrylic, urethane-acrylic, silicone, acylic-polyesters, epoxy-polyamide, polyvinyl acetate, vinyl-acrylic, silicone, silicone-acrylic, vinyl acetateethylene, styrene-acrylic, polyamide, hydrocarbon, vinyl acetate-acrylic and silane systems, and mixtures copolymers and terpolymers thereof for uses that requires a high level of aesthetics and appearance and that does not have disadvantages associated with coatings containing perfluorinated surfactants or trisiloxane surfactants.

Buffers, preservatives and other standard additives as known in the art can be included in the coating compositions of the invention in known and conventional amounts.

Solvents can be included in coating compositions of the present invention. Typically, the solvents are in a liquid state at room temperature. Suitable solvents include water, alcohols, aromatic solvents, oils (i.e. mineral oil, vegetable oil, silicone oil, and the like), lower alkyl esters of vegetable oils, fatty acids, ketones, glycols, polyethylene glycols, diols, paraffinics, and the like. In one specific embodiment of the invention, the solvent may be 2,2,4-trimethyl, 1-3-pentane diol, n-methyl-pyrrilidone or alkoxylated (especially ethoxylated) versions.

Co-surfactants can be included in the coating compositions of the present invention. According to one embodiment of the invention, typical co-surfactants include nonionic, cationic, anionic, amphoteric, zwitterionic, polymeric surfactants; or any mixture thereof. The co-surfactants are typically hydrocarbon based.

Moreover, other co-surfactants, that have short chain hydrophobes that do not interfere with super spreading as described in U.S. Pat. No. 5,558,806, incorporated by reference herein, are also useful.

Other useful co-surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; allyl polyglycosides; alkyl ethoxylated amines; and so forth.

In one embodiment of the invention, the amount of co-surfactant employed in the coating composition ranges from about 0.01 to about 5 weight percent of the total composition. In another embodiment of the invention, the amount of co-surfactant employed in the coating composition ranges from about 0.05 to about 2 weight percent of the total composition. In yet another embodiment of the invention, the amount of co-surfactant employed in the coating composition ranges from about 0.01 to 1 weight percent of the total composition.

Specific examples of co-surfactants include alkyl acetylenic diols (SURFONYL—Air Products), pyrrilodone based surfactants (e.g., SURFADONE—LP 100—ISP), 2-ethyl hexyl sulfate, isodecyl alcohol ethoxylates (e.g., RHODASURF DA 530—Rhodia), ethylene diamine alkoxylates (TETRONICS—BASF), ethylene oxide/propylene oxide copolymers (PLURONICS—BASF), Gemini type surfactants (Rhodia) and diphenyl ether Gemini type surfactants (e.g. DOWFAX—Dow Chemical).

In a specific embodiment of the invention, the co-surfactant is at least one selected from the group consisting of ethylene oxide/propylene oxide copolymers (EO/PO); amine ethoxylates; alkyl polyglycosides; and oxo-tridecyl alcohol ethoxylates.

When the subscript a of formula (1) satisfies the condition $2 \leq a \leq 5$, it is advisable to utilize a co-surfactant as hereinafter set forth in order to obtain the benefit of the compositions of the present invention.

The silylated polyether compounds (a) of the invention, as more fully described herein above, are used in the coating formulations in relatively small amounts. In one embodiment of the invention, the amount of silylated polyether compound (a) employed in the coating composition ranges from about 0.01 to about 5 weight percent of the total composition. Preferably, the amount of silylated polyether compound (a) employed in the coating composition ranges from about 0.05 to about 2 weight percent of the total composition. And most preferably, the amount of silylated polyether compound (a) employed in the coating composition ranges from about 0.01 to 1 weight percent of the total composition.

The silylated polyether compounds (a) of the invention can be used as solids, liquids, solutions or emulsions, depending on the nature and mode of application of the coating material.

Waterborne coatings often contain surfactants to stabilize the dispersion or to form the emulsions of the coating resin. The silylated polyether compound (a) should be compatible with the surfactants used to stabilize the dispersions or emulsions of the coating resin (b). Specifically, the silylated polyether compounds (a) should contain a very high level of oxyethylene units relative to the oxypropylene unit and oxybutylene units and $R^8$ groups that do not react with water. Preferred silylated polyether compounds suitable for waterborne coatings are those of formula (1) wherein $R^1$, $R^2$, $R^3$, $R^5$ and $R^6$ is methyl; $R^4$ is methylene or ethylene; $R^7$ is —CH$_2$CH$_2$CH$_2$O— or —CH$_2$CH(CH$_3$)CH$_2$O—; $R^8$ is hydrogen or methyl; and a is 1 to 20, b is 0 to 4; c is 0 to 4, with the proviso that a is greater than or equal to 5 times (b+c).

Preferred and non-limiting examples of silylated polyether compounds that are useful in waterborne coating compositions include, (CH$_3$)$_3$SiCH$_2$CH$_2$Si(CH$_3$)$_2$CH$_2$CH$_2$CH$_2$O (CH$_2$CH$_2$O)$_7$ CH$_3$, (CH$_3$)$_3$SiCH$_2$CH$_2$Si(CH$_3$)$_2$CH$_2$CH$_2$CH$_2$O(CH$_2$CH$_2$O)$_7$H, (CH$_3$)$_3$SiCH$_2$CH$_2$Si(CH$_3$)$_2$CH$_2$CH$_2$CH$_2$O(CH$_2$CH$_2$O)$_{20}$ CH$_3$,

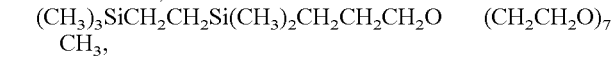

(CH$_3$)$_3$SiCH$_2$CH$_2$Si(CH$_3$)$_2$CH$_2$CH(CH$_3$)CH$_2$O(CH$_2$CH$_2$O)$_4$CH$_3$,

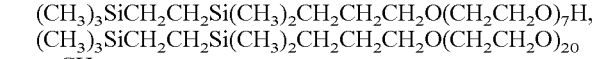

(CH$_3$)$_3$SiCH$_2$CH$_2$Si(CH$_3$)$_2$CH$_2$CH$_2$O(CH$_2$CH$_2$O)$_{10}$(CH$_2$CH(CH$_3$)O)$_1$CH$_3$, and

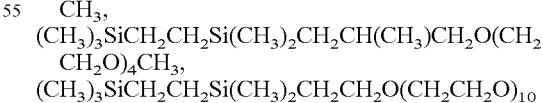

(CH$_3$)$_3$SiCH$_2$CH$_2$Si(CH$_3$)$_2$CH$_2$CH$_2$CH$_2$O(CH$_2$CH$_2$O)$_4$(CH$_2$CH(CH$_3$)O)$_1$CH$_3$.

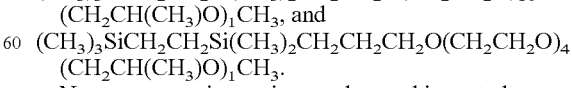

Numerous coating resins can be used in waterborne coating formulations, including polyester, acrylic, vinyl acrylics, polyurethane, vinyl acetate and the like. Emulsion lattices form films by evaporation of the water phase followed by coalescence of the polymer molecules. For the polymer to form a coherent film, the weight average molecular weight must be sufficiently high, preferably greater than 20,000 gram per mole, more preferably from 50,000 grams per mole to 2,000,000 grams per mole, and most preferably, from 75,000 gram per mole to 500,000 gram per mole. In addition, the glass transition temperature of the coating resins, referred to as Tg, must be above the minimum film forming temperature (MFFT) of the coating composition. The Tg of the coating resin is preferably less than 40° C., more preferably from −20° C. to 35° C. and most preferably from 0° C. to 20° C.

Preferred waterborne coating resins are acrylic resins. The acrylic resins can contain reactive functional groups including carboxylate, epoxy, hydroxyl, amine, amide or vinyl. Useful monomers in the preparation of acrylic resins include, but are not limited to, acrylonitrile, acrylic acid, methyl acrylate, ethyl acrylate, butyl acrylate, 24 ethylhexyl acrylate, methoxyethyl acrylate, diaminoethyl acrylate, methacrylic acid, methyl methacrylate, ethyl methacrylate, isobutyl methacrylate, 2-ethylhexyl methacrylate, lauryl methacrylate, stearic methacrylate, dimethylaminoethyl methacrylate, 2-hydroxylpropyl acrylate, 2-hydroxylpropyl methacrylate, acrylamide, methacrylamide and glycidyl acrylate.

The acrylic resins can also contain co-monomers that contain reactive groups, such as carbon-carbon double bonds or carbon-carbon triple bonds. Typical non-limiting co-monomers include styrene, vinyl acetate, vinyl chloride, vinyl alcohol and the like.

The preparation of acrylic resins is described in "Waterborne & Solvent Based Acrylics and their End User Applications", P. Oldring, and P. Lam (eds.), John Wiley & Sons, New York 1997, and is incorporated by reference herein in its entirety.

Representative, non-limiting examples of acrylic resins include commercially available styrene acrylic emulsion polymers, such as JONCRYL® 554, JONCRYL® 540, JONCRYL® 77, and JONCRYL® 95, and SCX 2500, all commercially available from SC Johnson Polymer of Racine, Wis. Other specific examples of commercially available preferred reactive polymers materials which can be used include NEOCRYL® acrylic emulsions, NEOREZ® water-borne urethane polymers and NEOPAC® water-borne urethane acrylic copolymers, available from ZENECA Resins of Wilmington, Mass., and UCAR® acrylic and vinyl acrylic latexes available from Dow Corporation of Midland, Mich.

Radiation-curable coating compositions of the present invention can contain a variety of coating resins that cure upon exposure to radiation, such as ultra-violent or electron beam radiation. Such coating resins include epoxy acrylates, polyester acrylates, acrylated epoxidized vegetable oils, fatty acid modified acrylates and epoxides. The resin polymers are highly viscous in the neat or 100 percent active form and cannot be applied without diluting them with a diluent to reduce the viscosity. The diluents are either solvents or reactive monomeric compounds, referred to as reactive diluents. Typical, non-limiting diluents include mono-acrylates, diacrylates, tri-acrylates and poly-acrylates. Representative non-limiting examples of reactive diluents include dipropyleneglycol diacrylate, tripropyleneglycol di-acrylate, 1,6-hexanediol diacrylate, ethoxylated bisphenol-A diacrylate, pentaerythritol triacrylate, trimethylolpropanetriacrylate, propoxylated glycerol triacrylate, trimethylolpropane tetraacrylate, di-pentaerythritol pentaacrylate and di-pentaerythritol hexaacrylate.

Silylated polyether compounds (a) useful in the radiation-curable coating compositions are soluble in the mixture of the coating resin and reactive diluent. Spedifically, the silylated polyether compounds (a) should contain a mixture of oxyethylene units and oxypropylene or oxybutylene units. Preferred silylated polyether compounds suitable for radiation cured coatings are those of formula (I) wherein $R^1$, $R^2$, $R^3$, $R^5$ and $R^6$ is methyl; $R^4$ is methylene, ethylene or propylene; $R^7$ is —$CH_2CH_2CH_2O$— or —$CH_2CH(CH_3)CH_2O$—; $R^8$ is hydrogen, methyl or acetyl; and a is 2 to 10, b is 2 to 10; c is 0 to 10, with the proviso that ratio, a/b+c is from 0.1 to 5, preferably from 0.5 to 2 and most preferably 1 to 1.5.

Representative and non-limiting examples of the silylated polyether compound (a) for radiation-curable coating compositions include

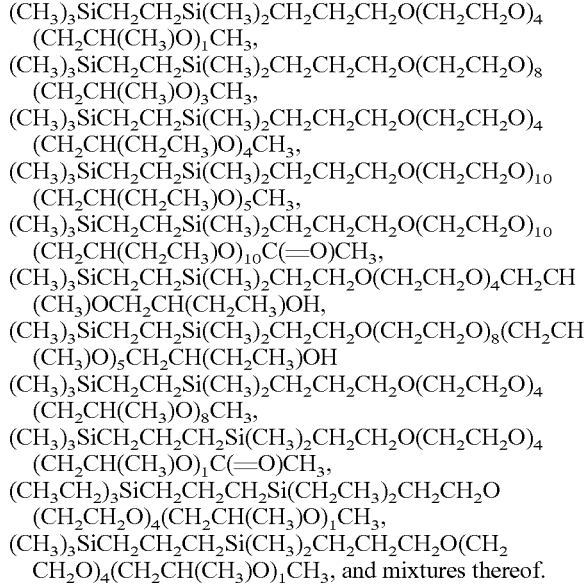

$(CH_3)_3SiCH_2CH_2Si(CH_3)_2CH_2CH_2CH_2O(CH_2CH_2O)_4$
  $(CH_2CH(CH_3)O)_1CH_3$,
$(CH_3)_3SiCH_2CH_2Si(CH_3)_2CH_2CH_2CH_2O(CH_2CH_2O)_8$
  $(CH_2CH(CH_3)O)_3CH_3$,
$(CH_3)_3SiCH_2CH_2Si(CH_3)_2CH_2CH_2CH_2O(CH_2CH_2O)_4$
  $(CH_2CH(CH_2CH_3)O)_4CH_3$,
$(CH_3)_3SiCH_2CH_2Si(CH_3)_2CH_2CH_2CH_2O(CH_2CH_2O)_{10}$
  $(CH_2CH(CH_2CH_3)O)_5CH_3$,
$(CH_3)_3SiCH_2CH_2Si(CH_3)_2CH_2CH_2CH_2O(CH_2CH_2O)_{10}$
  $(CH_2CH(CH_2CH_3)O)_{10}C(=O)CH_3$,
$(CH_3)_3SiCH_2CH_2Si(CH_3)_2CH_2CH_2O(CH_2CH_2O)_4CH_2CH$
  $(CH_3)OCH_2CH(CH_2CH_3)OH$,
$(CH_3)_3SiCH_2CH_2Si(CH_3)_2CH_2CH_2O(CH_2CH_2O)_8(CH_2CH$
  $(CH_3)O)_5CH_2CH(CH_2CH_3)OH$
$(CH_3)_3SiCH_2CH_2Si(CH_3)_2CH_2CH_2CH_2O(CH_2CH_2O)_4$
  $(CH_2CH(CH_3)O)_8CH_3$,
$(CH_3)_3SiCH_2CH_2CH_2Si(CH_3)_2CH_2CH_2O(CH_2CH_2O)_4$
  $(CH_2CH(CH_3)O)_1C(=O)CH_3$,
$(CH_3CH_2)_3SiCH_2CH_2CH_2Si(CH_2CH_3)_2CH_2CH_2O$
  $(CH_2CH_2O)_4(CH_2CH(CH_3)O)_1CH_3$,
$(CH_3)_3SiCH_2CH_2CH_2Si(CH_3)_2CH_2CH_2CH_2O(CH_2$
  $CH_2O)_4(CH_2CH(CH_3)O)_1CH_3$, and mixtures thereof.

Other optional components of radiation-curable coating compositions of the present invention include non-reactive diluents, photoinitiators and photosynerists, pigments and the like. A description of these other components and formulations containing them is described in "Chemistry & Technology of UV & EB Formulation for Coatings, Inks & Paints", vol. IV, C. Lowe, G. Webster, S. Kessel and I. McDonald, John Wiley & Sons, New York, 1997, and is incorporated by reference herein in its entirety.

High solids coatings and solvent-borne coatings require silylated polyether compounds that are soluble in the coating resin and solvent mixtures. The silylated polyether compounds (a) suitable for the use in these formulations are those previously described for radiation-cured coatings.

Coating resins (b) suitable for use in high solids coatings and solvent-borne coatings include epoxide resins, solvent based polyacrylates, polyisocyanate resins, and polyurethane resins. Specific acrylic and epoxy resins are described in H. Coyard, P. Deligny, N. Tuck, "Resins for Surface Coatings Acrylics & Epoxies", vol I, $2^{nd}$ ed., P. Oldring (ed.), John Wiley & Sons, New York, 2001, and is incorporated by reference herein in its entirety.

Powder coatings are particulate solid materials that coalescence upon application. Because the physical form of the coating is a solid, leveling and flow properties are very poor. Typical coating resins (b) for powder coating compositions are thermoplastic resin or thermosetting resins. Thermoplastic resins include polyvinyl chloride, thermoplastic polyester, polyethylene, polypropylene, and polyamide. Thermosetting resins include epoxy resin, unsaturated polyether resins and acrylic polymers. The weight average molecular weight for thermoplastic coating resins is from 10,000 to 2,000,000 grams per mole, and preferably, 30,000 to 250,000 gram per mole. The weight average molecular weight for thermosetting coating resins are from 1,000 to 10,000 grams per mole, and preferably 3,000 to 6,000 grams per mole. Power coating resins are described in T. A. Misev, "Powder Coatings Chemistry and Technology, John Wiley & Sons, New York, 1991, and is incorporated by reference herein in its entirety.

Silylated polyether compounds (a) suitable for powder coatings are preferably solid materials. Preferred silylated polyether compounds suitable for powder coating compositions are those of formula (1) wherein $R^1$, $R^2$, $R^3$, $R^5$ and $R^6$ is methyl; $R^4$ is methylene, ethylene or propylene; $R^7$ is —$CH_2CH_2CH_2O$— or —$CH_2CH(CH_3)CH_2O$—; $R^8$ is hydrogen, methyl or acetyl; and a is from 15 to 40; b is from 0 to 2; c is 0, with the proviso that ratio, b/a is from 0 to 0.15, and preferably 0.

Representative and non-limiting examples of silylated polyether compounds (a) suitable for powder coatings include

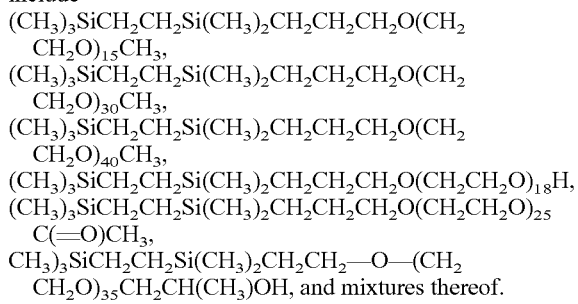

Printing Inks

Printings inks and graphic arts products are homogeneous products which contain pigments, dyes or any kind of coloring matter that can be used to provide aesthetic or functions to printed materials. These functions include visibility, rheology, light fastness and other parameters useful for product identification or protection. Pigments can be treated in order to be sustained in homogeneous form that will allow their transfer from liquid to solid with appropriate printing equipment. To do so vehicles constituted of binders and solvents can be used to provide the necessary flow to the ink composition. The printing technologies used can affect the possible use of binders and solvents used to manufacture the ink.

The silylated polyether compounds (a) of the invention, as more fully described herein above, are used in the ink formulations in relatively small amounts. In one embodiment of the invention, the amount of silylated polyether compound (a) employed in the ink composition ranges from about 0.01 to about 5 weight percent of the total composition. Preferably, the amount of silylated polyether compound (a) employed in the ink composition ranges from about 0.05 to about 2 weight percent of the total composition. And most preferably, the amount of silylated polyether compounds (a) employed in the ink composition ranges from about 0.01 to 1 weight percent of the total composition.

Ink technologies can be divided broadly into the following categories: lithographic process (to which belong lithography and offset technologies); typographic process (to which belong flexography) or gravure process (to which belong gravure technologies); and Non Impact Process and Digital Imaging systems which are applied in particular in computerized edition. It is noticeable that in all the processes involved one of the most critical issues is the transfer from a liquid ink to solid state onto substrate of various nature that have very different surface activities. Thus, in printing inks systems, surface activity of the liquid and solids is an important part of the quality of printing.

In liquid inks, applied by either flexographic or gravure processes, ink technologies can be quite similar in terms of composition and mainly differ by the specifications of inks in terms of viscosity, solvent type, pigment concentration and other parameters induced by the end use application.

Liquid inks can be divided into solvent-borne, radical curing (UV) or waterborne systems.

The nature of the solvent used will obviously affect the binder and polymer selection used to design the inks. In solvent-borne systems low boiling point alcohols and esters will be used. The type of resins used are therefore selected to be soluble in these solvents. The most common grades are nitrocellulosic, polyurethanes, acrylics soluble, polyamides, ketonic or maleic resins, polyvinyl chlorides, epoxies, isocyanates, polyvinyl butyral and the like.

In waterborne systems, solvent being mainly water, the resins are typically designed in a way that they can be diluted or soluble in water but once applied should be resistant to water and humidity. This apparent contradiction has been overcome by use of anionic (or cationic) based polymers that have the ability to release and/or block their hydrophilic or hydrosoluble moiety upon drying. Also curing polymers are used based on nonionic polymer cured with appropriate curing agents like isocyanates or epoxy resins or melamines. Typical products include acrylic and styrene acrylic emulsions or latexes, polyurethane dispersions, epoxy dispersions, polyacrylates, polyvinylic dispersions, soluble polyamides or maleic resins and the like.

Radical curing inks (UV) typically do not typically contain solvents but are mainly constituted of low molecular weight polymers or oligomers diluted with monomers when necessary. The different components are selected so that components cure under radical polymerization upon exciting with UV lamps in association with photo initiators. Typical polymers include acrylates, epoxy acrylates, urethane acrylates, polyesters acrylates and their relative monomers bearing unsaturation, especially carbon-carbon double bonds or carbon-carbon triple bonds.

Pigments, thickeners and other standard additives as known in the art can be included in printing ink compositions of the invention in known and conventional amounts.

In liquid inks the pigments, fillers or particulates giving the visual aspect of the inks should be very well dispersed and grinded in order to reach appropriate flow and leveling on the substrates and during transfer from the press. To do so, surface-active dispersing agents or binders acting as polymeric dispersants are typically used. Specific grades of the resins mentioned above have the ability to properly disperse and sustain pigments in the appropriate form. Surface-active agents of many different natures may also be used to disperse pigments. Anionic dispersants like alkyl phosphates, sulphonates or sulfates and the like), cationic dispersant (like quaternary ammoniums), amphoteric dispersant (like betaines, or alkyl ethoxylates (like formerly used nonyl phenol ethoxylate, alcohol ethoxylates and the like) are particularly useful. Because of their chemical structure and the electrostatic method of stabilization of the pigment particles, surfactants may cause different defects, such as water sensitivity, foam formation, interference with intercoat adhesion. Surface-active agents may compensate or minimize these defects.

Other ingredients may be used to achieve the properties required by the ink such as transfer of the ink from printing unit, wetting of substrates, adhesion, specific resistances (like thermal or chemical resistances) or properties (like gloss).

Besides the binders, additional ingredients may be provided that have other functions, such as defoamers (active to reduce foam) or antifoam (active to prevent foam formation). Suitable defoamers include non-silicone-based defoamers. Silicones are often avoided because silicone materials can lead to multiple drawbacks among which fish eyes are the most critical one. Non-silicone based defoamers contain mainly mineral oil based materials and non-mineral based materials which may be emulsified with hydrophobic solids.

As defoamers may create leveling and wettability problems, the use of wetting agents or spreaders can minimize or suppress these effects. Typical leveling and wetting agents include also silicone-based and non-silicone based surfactants. Typical non-silicone based materials include diethylenic surfactants, alkyl surfactants and alkyl aryl ethoxylate surfactants.

Printing inks of the present invention may also contain ingredients that can reduce or adjust coefficient of friction (COF) using non-silicone based additives. The non-silicone based additives are natural, chemical or petroleum derivatives like natural waxes, (carnauba waxes and the like), olefinic waxes (PE or PP waxes), chemical waxes (amides). Other additives may include plasticizers (like phathlates, phosphates), glycols and coalescing agents. Silicone-based additives and fluorinated waxes are less desirable.

Glycols and coalescing agents may also be used in waterborne inks that are designed to modify film formation temperature or drying speed. Useful coalescing agents include oxide-based glycol ether solvents, such as ethylene glycol monomethyl ether, ethylene glycol monoethyl ether, ethylene glycol monopropyl ether, butyl carbitol, dipropylene glycol dimethyl ether, and butyl glycol, butyldiglycol, and ester-based solvents such as ethylene glycol monobutyl ether acetate, diethylene glycol monoethyl ether acetate, methoxypropylacetate and butyl cellosolve actetate.

Printing ink compositions of the present invention may also include adhesion promoters. Among these the most classical known products are chelates of titanates, including titanium acetyl acetonate; zirconium salts, including zirconium carbonates or propionates; zinc oxides solutions; polyaziridines (though carcinogenic materials); organofunctional silanes including silane gamma-glycidoxypropyltrimethoxysilane, gamma-glycidoxypropyltriethoxysilane and gamma-glycidoxypropylmethyldiethoxysilane, beta-(2-aminoethyl)-gamma-aminopropyltrimethoxysilarie; and imines, such as polyethylene imine.

Numerous other additives may also include optical brighteners, humectants (urea or phenols based material to avoid skin drying), UV absorbers (for light stability), rheological agents (thixotropic or sag reducing agents or thickeners), amines (for pH adjustments), biocides and the like.

A typical waterborne ink formulation is as follows: Organic pigment dispersion made with surfactant or acrylic solution resin in water; Polymer emulsion (styrene acrylic or urethane dispersion); Acrylic solution resin; Polyethylene wax dispersion; Antifoam; Wetting agent; Thixotropic agent; Thickener; Coalescing agent; Alcohol; and Water.

Preparation of Coating or Ink Compositions

The coating or ink compositions of the present invention may be prepared by methods known in the art.

Although the order of addition is not critical, typical procedures for preparing waterborne coatings involve charging a high-speed or low-speed mixer with solvent, dispersant, antifoam, pigments, extender and filler, grinding the materials at high speed, and then letting down the mixture with coating resin (b) or ink resin (b), coalescent agent, preservatives, buffer, wetting agents and the silylated polyether compound of the present invention.

High speed mixing can be carried out using a high-speed mixer, such as a Cowles mixer, from 1 to 60 minutes, preferably 5 to 30 minutes and most preferably for 15 to 25 minutes at a temperature of between 5 and 80 degrees Centigrade. Low speed mixing is typically a blade mechanical stirrer.

A stripping, sparging or distilling of the coating or ink composition can be used to remove hazardous air pollutants (HAP or HAPS) and volatile organic compounds (VOCs). Additional water or other non-volatile components can be added to the coating or ink composition to replenish any water or other non-volatile components removed during the stripping, sparging or distilling step.

Coating or ink compositions that are substantially free of hazardous air pollutants (HAP or HAPS) and volatile organic compounds (VOCs) are advantageous. Hazardous air pollutant and volatile organic compounds pose health and safety risks for the workers coming in contact with the coating or ink composition, contribute to air pollution, and often require permitting of the manufacturing facility by the local governmental agencies.

Hazardous air pollutants are any compounds used in coatings or inks that have been identified as such in the Clean Air Act Amendments of 1990. Hazardous air pollutants can be stabilizing agents, solvents, or other components incorporated into the conversion or passivation coatings. The Clean Air Act Amendments of 1990 identified hazardous air pollutants, which include acetamide, acrylamide, acrylic acid, acrylonitrile, allyl chloride, aniline, benzene, 1,3-butadiene, caprolactam, catechol, cumene, 1,2-dichloroethane, dichloroethyl ether, diethanolamine, dimethylamino-azobenzene, dimethylfomamide, dimethylphthalate, epichlorohydrin, ethyl acrylate, ethyl benzene, ethylene dibromide, ethylenimine, formaldehyde, hexachlorobenzene, n-hexane, hydroquinone, isophorone, maleic anhydride, methanol, methyl ethyl ketone, methyl isobutyl ketone, methylene chloride, naphthalene, nitrobenzene, 2-nitropropane, pentachlorophenol, phenol, propylene oxide, styrene, 1,1,2,2-tetrachloroethane, toluene, 2,4-toluene diisocyanate, 1,1,1-trichloroethane, trichloroethylene, 2,4,6-trichlorophenol, vinyl acetate, vinyl chloride, xylenes, m-xylene, o-xylene, p-xylene and combinations thereof.

"Substantially free of hazardous air pollutant" refers to a level of hazardous air pollutant of specifically less than about 1 weight percent, more specifically less than about 0.2 weight percent, even more specifically less than about 0.05 weight percent and most specifically less than about 0.01 weight percent, said weight percents being based on the total weight of the composition.

Volatile organic compound (VOC) is any organic compound, which participates in any atmospheric photochemical reactions and includes all volatile organic compounds except those compounds that the Environmental Protection Agency (EPA) has designated as having negligible photochemical reactivity. Typical volatile organic compounds include methanol, ethanol, n-propanol, 2-propanol, n-butanol, 2-butanol, tert-butanol and combinations thereof.

Low in volatile organic compounds is a level of specifically less, than about 10 weight percent, more specifically less than about 5 weight percent, even more specifically less than about 2 weight percent and most specifically less than about 1 weight percent, said weight percents being based on the total weight of the composition, of volatile organic compounds in the coating or ink composition. The amount of volatile organic compound in coatings is calculated according to EPA Method 24 from percent non-volatile, with corrections on exempt solvents and water. The non-volatile content is measured based on ASTM Standards D2369 and D3960. Typically, a sample of material is placed in a dish and placed in a convection oven at 110° C. for 1 hour. The weight remaining in the dish is then determined.

Power coatings are prepared in a multi-step process comprising the steps of premixing the components, hot melt compounding, cooling, granulation, fine grinding and classifying. Typically, the coating resin (b), pigments, fillers, additives, hardeners and silylated polyether compound (a) are premixed. Tumbler mixers, double cone blenders, horizontal mixers, high-speed blenders and conical mixers are all suitable for preparing the premix. The hot melt compounding involves charging the premix to the compounding machine, which converts the premix into a molten phase and disperses the fillers and pigments. Extruders, Z-blade mixers and heated twin-roll mills can be used. The components are processed at temperatures ranging from 50° C. to 180° C. for 1 minutes to 10 hours, more preferably from 70° C. to 150° C. for 2 minutes to 4 hours, and most preferably from 110° C. to 130° C. for 10 minutes to 2 hours. After the compounding, the powder coating composition is cooled and squeezed between chill rolls, forming an easily breakable continuous strip and flaking by a kibler unit. The flaked composition is formed into fine particles in a fine grinding process. The grinding process can be accomplished by hammer mills, pin disc mills ZSP Circoplex classifier mills opposed jet mills and the like. The particle size classification is accomplished using a classifying mill, air stream classification, sieving using tumbler screening machines, vibratory screening machines, pneumatic tumbler screening and centrifugal sifters.

Method for Treating Surfaces using Compositions of the Present Invention

The methods for treating surfaces with the coating or ink compositions of the present invention are known in the art. Coatings and inks can be applied using a variety of methods including spraying, bushing, dipping, electro-deposition, spin coating, transfer printing and the like.

EXAMPLES

The invention will now be described in conjunction with the following examples which are to be regarded as being illustrative of certain embodiments of the invention but should not be viewed to restrict the invention.

Example 1

Preparation of Silicon-Based Polyether Copolymer $(CH_3)_3Si(CH_2)_2Si(CH_3)_2CH_2CH_2CH_2O(CH_2CH_2O)_{7.5}CH_3$ A 200 mL round-bottom flask was equipped with a magnetic stir bar, reflux condenser w/$N_2$ inlet, thermocouple, addition funnel and heating mantle. Vinyltrimethylsilane (25.7 grams, 0.257 mole) and Karstedt's catalyst (10 ppm) were charged to the flask, and brought to 30° C. under $N_2$. Dichloromethylsilane (24.3 grams, 0.257 mole) was charged to the addition funnel, and added dropwise to the round-bottom flask. An immediate was exotherm noted, and addition continued over 1 hour. After addition, the reaction was maintained at 40° C. for 1 hour, and then analyzed by GC. We found >98% conversion to pentamethylchlorodicarbodisilane. The product was taken up in toluene (100 grams), charged to a 500-mL round-bottom flask, and the solution was cooled to 0° C.

A solution of sodium dihydro-bis-(2-methoxyethoxy) aluminate (Vitride, 70% in toluene; 39.3 grams of solution, 0.135 mole) was charged to an addition funnel and added dropwise to the solution at a rate to maintain reaction temperature <5° C. (total addition ~0.2 hours). After complete addition, the reaction was allowed to warm to room temperature, and was stirred an additional 2 hours. A reaction sample was taken, neutralized and analyzed by GC; we found quantitative conversion to pentamethyldicarbosilane reduction product. The reaction mixture was neutralized slowly with 0.5N HCl, then extracted with water (3×100 milliliters) and dried over $Mg_2SO_4$, filtered and bottled as 22% solution in toluene (110 grams).

A 200-mL round-bottom flask was equipped with a magnetic stir bar, reflux condenser w/$N_2$ inlet, thermocouple, addition funnel and heating mantle. Allyl-started, methyl-capped polyethylene oxide, $(CH_2=CHCH_2—O—(CH_2CH_2O)_{7.5}CH_3$; 33.7 grams; 0.0810 mole), chloroplatinic acid (10 ppm) and sodium propionate (50 milligrams) were charged to the round-bottom flask, stirred and brought to 80° C. The solution of silane in toluene (45.5 grams of 22% solution; 10.0 grams, 0.0623 mole) was charged to the addition funnel and added dropwise to the flask. A minor exotherm was noted, and addition continued over 45 min. After complete addition, the reaction was maintained at 85° C. for 1 hour. A reaction sample was tested for Si—H content, and 0 cc $H_2$/gram was found remaining. The mixture was stripped (~10 millimeters Hg, 100° C.) for 1.5 hours to remove toluene, allowed to cool to <40° C., treated with Celite and sodium bicarbonate, stirred, pressure filtered, and bottled. The yield was 42.1 grams of clear, pale yellow fluid.

Example 2

Preparation of Silicon-Based Polyether Copolymer
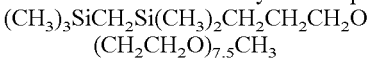

The Grignard reagent of trimethylchloromethylsilane was prepared by reacting trimethylchloromethylsilane (12.3 grams, 0.1 mole) with magnesium chips (2.88 grams, 0.12 mole) in tetrahydrofuran (50 milliliters. The Grignard reagent was then added dropwise into dimethylchlorosilane (9.46 grams 0.1 mole), which was dissolved in tetrahydrofuran (50 milliliters). The mixture was stirred at room temperature overnight, quenched with hydrochloric acid solution (20 milliliters), and extracted with diethyl ether (100 milliliters). The organic layer was washed with distilled water three times and dried with anhydrous sodium sulfate. The mixture was purified by distillation at 118-119° C. to yield (trimethylsilylmethyl)dimethylsilane product (13.0 grams, 89% yield) as a clear, colorless liquid.

The (trimethylsilylmethyl)dimethylsilane was reacted with allyl-started, methyl-capped polyethylene oxide, $(CH_2=CHCH_2—O—(CH_2CH_2O)_{7.5}CH_3$, according to procedures similar to Example 1.

Example 3

Preparation of Silicon-Based Polyether Copolymer
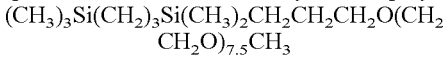

Trimethylallyl silane (11.4 grams, 0.1 mole), dimethylchlorsilane (9.5 grams, 0.1 mole) and 10 microlillter of platinum(0)-1,3-divinyl-1,1,3,3-tetramethyldisiloxane complex (0.1 molar in xylene) were charged into a 100-milliliter three-neck round bottom flask equipped with nitrogen gas inlet and condenser. The mixture was stirred at room temperature for 30 minutes and heated to 70° C. for 2 hours. The reaction was monitored using a $^1$H NMR method. After cooling to room temperature, tetrahydrofuran (50 milliliters) was added and the solution was cooled to −80° C. Lithium aluminum hydride (1.0 grams) was added to the solution and stirred until the mixture warmed up to room temperature. The mixture was stirred at room temperature overnight. Hydrochloric acid solution (10 milliliters) was added to quench the reaction and the organic layer was separated and washed three times with water and dried over anhydrous sodium sulfate. The mixture was purified by vacuum distillation, collected at 60-61° C. at 1 to 2 millimeters of Hg to yield (3-(trimethylsilyppropyl) dimethylsilane 912.3 grams, 70.7% yield) as a clear, colorless liquid.

The (3-(trimethylsilyl)propyl)dimethylsilane was reacted with allyl-started, methyl-capped polyethylene oxide, $(CH_2=CHCH_2—O—(CH_2CH_2O)_{7.5}CH_3$, according to procedures similar to Example 1.

Example 4

Preparation of Silicon-Based Polyether Copolymer $(CH_3)_3Si(CH_2)_2Si(CH_3)_2CH_2CH_2CH_2O(CH_2CH_2O)_{25}CH_3$ The (trimethylsilylethyl)dimethylsilane is reacted with allyl-started, methyl-capped polyethylene oxide, $(CH_2=CHCH_2—O—(CH_2CH_2O)_{25}CH_3$, according to procedures similar to Example 1.

Example 5

Preparation of Silicon-Based Polyether Copolymer $(CH_3)_3SiCH_2CH_2Si(CH_3)_2CH_2CH_2CH_2O(CH_2CH_2O)_{10}(CH_2CH(CH_2CH_3)O)_5CH_3$ The (trimethylsilylethyl)dimethylsilane is reacted with allyl-started, methyl-capped polyethylene oxide, $(CH_2=CHCH_2—O—(CH_2CH_2O)_{10}(CH_2CH(CH_2CH_3)O)_5CH_3$, according to procedures similar to Example 1.

Examples 6-8, Comparative Examples 9-12

Surface Tension and Spreading Properties

Table 1 provides a description of the comparative trisiloxane polyether and organosilicone-based polyether compounds of the general structure:

$MD_xD'_yM$ where M is $(CH_3)_3SiO_{1/2}$; D is $(CH_3)_2SiO_{2/2}$ and D' is $CH_3Si(CH_2CH_2CH_2O)—(CH_2CH_2O)_{7.5}R$.

TABLE 1

Composition of Comparative Organosilicone Polyether Surfactants

|  | x | y | R |
|---|---|---|---|
| Comparative Example 9 | 0 | 1 | $CH_3$ |
| Comparative Example 10 | 0 | 1 | H |
| Comparative Example 11 | 20 | 3 | $CH_3$ |

Additionally, Comparative Example 12 is OPE, an octylphenolethoxylate, containing 10 polyoxyethylene units, and is a non-silicone organic surfactant. This product is available as Triton® X-100 from Dow Chemical Company, Midland, Mich.

Table 2 demonstrates the ability of the silylated polyether compounds of the present invention to reduce aqueous surface tension thereby showing utility as surfactants. Surface tension was measured using a Kruss surface tensiometer, with a sand blasted platinum blade as the sensor. Solutions of the various components were prepared at 0.1 wt % in 0.005M NaCl water (deionized), as an equilibrium aid.

Table 2 displays solutions of these compositions provide a significant reduction in surface tension relative to the conventional surfactant.

The compositions of the present invention also provide spreading properties similar to the Comparative Examples 9 and 10. Additionally, silylated polyether compounds of the present invention provide improved spreading relative to the conventional silicone polyether Comparative Example 11 and conventional organic surfactant Comparative Example 12.

Spreading was determined by applying a 10 μL droplet of surfactant solution to polyacetate film (USI, "Crystal Clear Write on Film") and measuring the spread diameter (mm) after 30 seconds, at a relative humidity between 50 and 70% (at 22 to 25° C.). The solution was applied with an automatic pipette to provide droplets of reproducible volume. Deionized water that was further purified with a Millipore filtration system was used to prepare the surfactant solutions.

TABLE 2

Surface Tension and Spreading Properties

| Compound | Surface Tension mN/m | Spread Diameter (mm) Weight % Surfactant | | | |
|---|---|---|---|---|---|
|  |  | 0.05% | 0.1% | 0.2% | 0.5% |
| Example 1 | 24.6 | 27 | 44 | 44 | 45 |
| Example 2 | 24.2 | 24 | 41 | 43 | 45 |
| Example 3 | 23.8 | 28 | 44 | 44 | 39 |
| Comparative Example 9 | 20.9 | 34 | 53 | 51 | 25 |
| Comparative Example 10 | 20.6 | 37 | 53 | 50 | 35 |
| Comparative Example 11 | 23.6 | nd[1] | nd[1] | nd[1] | 6 |
| Comparative Example 12 | 31.8 | nd[1] | 9 | nd[1] | 10 |

[1]nd means not determined.

Hydrolytic stability was determined for representative compositions of the present invention using HPLC. Solutions of the various compositions were prepared at 0.5 wt % over a pH range from pH 4 to pH 11, and monitored by HPLC for decomposition as a function of time.

Analytical Method

The samples were analyzed by a reverse-phase chromatographic technique using the experimental conditions listed in Table 3.

TABLE 3

Solvent Gradient for HPLC Method

| Time (min.) | % Methanol | % Water | % Isopropanol |
|---|---|---|---|
| 0.0 | 70 | 30 | 0 |
| 15.0 | 100 | 0 | 0 |
| 20.0 | 50 | 0 | 50 |
| 20.1 | 70 | 30 | 0 |
| 25.0 | 70 | 30 | 0 |

Detector: ELSD/LTA (Evaporative Light Scattering with Low Temperature Adapter
Conditions: 30° C., 1.95 SLPM $N_2$
Column: Phenomenex LUNA C18 end cap, 5 micron, 75 × 4.6 mm
Flow Rate: 1.0 mL/min.
Inj. Volume: 1.0 microlitres
Sample: 0.050 g/mL in methanol Tables 4-6 demonstrate that the silylated polyether compounds of the present invention provide improved resistance to hydrolytic decomposition relative to the standard siloxane based surfactant Comparative Example 9, under similar pH conditions.

Comparative Example 9 shows rapid hydrolysis at pH values below 5 and at pH values above 9, while the present invention demonstrates a higher resistance to hydrolysis under the same conditions.

TABLE 4

Hydrolytic Stability of Silylated Polyether Compound by HPLC

|  |  | Stability: % Silylated Polyether Compound Remaining | | | | | |
|---|---|---|---|---|---|---|---|
|  | Time | pH 2 | pH 4 | pH 5 | pH 7 | pH 9 | pH 12 |
| Example 1 | 24 h | nd[1] | 100 | 100 | 100 | 100 | nd[1] |
| Example 1 | 1 wk | 100 | 100 | 100 | 100 | 100 | 77 |
| Example 1 | 2 wk | nd[1] | 100 | 100 | 100 | 100 | nd[1] |
| Example 1 | 3 wk | 100 | nd[1] | nd[1] | nd[1] | nd[1] | 77 |
| Example 1 | 4 wk | nd[1] | 100 | 100 | 100 | 100 | nd[1] |
| Example 1 | 7 wk | 100 | 100 | 100 | 100 | 100 | 74 |
| Example 1 | 12 wk | 86 | 100 | 100 | 100 | 100 | 74 |
| Example 1 | 19 wk | 79 | 87 | 100 | 100 | 100 | 77 |
| Example 1 | 30 wk | 73 | 79 | 90 | 94 | 97 | 75 |

[1]nd means not determined.

TABLE 5

Hydrolytic Stability of Silylated Polyether Compound by HPLC

|  |  | Stability: % Silylated Polyether Compound Remaining | | | | | |
|---|---|---|---|---|---|---|---|
|  | Time | pH 2 | pH 4 | pH 5 | pH 7 | pH 9 | pH 12 |
| Example 2 | 24 h | nd[1] | 100 | 100 | 100 | 100 | nd[1] |
| Example 2 | 1 wk | 100 | 100 | 100 | 100 | 100 | 77 |
| Example 2 | 2 wk | nd[1] | 100 | 100 | 100 | 100 | nd[1] |
| Example 2 | 3 wk | nd[1] | nd[1] | nd[1] | nd[1] | nd[1] | 73 |
| Example 2 | 4 wk | nd[1] | 100 | 100 | 100 | 100 | nd[1] |
| Example 2 | 7 wk | 89 | 100 | 100 | 100 | 100 | 76 |
| Example 2 | 12 wk | 95 | 100 | 100 | 100 | 100 | 76 |
| Example 2 | 19 wk | 95 | 87 | 100 | 100 | 100 | 72 |
| Example 2 | 30 wk | 73 | 100 | 100 | 100 | 100 | 74 |

[1]nd means not determined.

TABLE 6

Hydrolytic Stability of Comparative Siloxane Based Surfactants by HPLC

|  |  | Stability: % Siloxane Surfactant Remaining | | | | |
|---|---|---|---|---|---|---|
|  | Time | pH 4 | pH 5 | pH 7 | pH 9 | pH 10 |
| Comparative Example 9 | 24 h | 50 | 93 | 100 | 95 | 75 |
| Comparative Example 9 | 48 h | 22 | 85 | 100 | 88 | 52 |
| Comparative Example 9 | 1 wk | 0 | 58 | 100 | 72 | 12 |

Unlike traditional siloxane based surfactants, which are subject to rapid hydrolysis under acidic and basic conditions (at pH values of 5 or below and at pH values of 5 or above) the silylated polyether compounds of the present invention provide increased resistance to hydrolysis relative to traditional trisiloxane alkoxylates (e.g., Comparative Example 9). An artifact of hydrolysis is observed as a reduction in spreading properties over time. Therefore solutions of the organomodified trisiloxane surfactants (i.e., Example 3) of the present invention, as well as Comparative Example surfactants (i.e., Comparative Example 9) were prepared at desired use levels and pH. Spreading was determined as a function of time to illustrate resistance to hydrolysis.

Table 7 contains illustrative examples of traditional organomodified trisiloxane ethoxylate surfactants, which exhibit decreased spreading performance with time as a function of hydrolytic decomposition over a pH range from pH 3 to pH 10. Here, a 0.4 weight percent solution of comparative Example 9 was prepared at pH 3, 4, 5 and 10. Spreading was determined according to the procedure described above.

Table 7 also contains an illustrative example of a silylated polyether compound of the present invention, where the product of Example 1 has improved resistant to hydrolysis over a pH range from pH 3 to pH 10 relative to the traditional trisiloxane ethoxylate surfactant of Comparative Example 9.

TABLE 7

Effect of pH on Spreading Properties Vs Time of Comparative Example 7.

|  |  | Spread Diameter (mm) | | | |
|---|---|---|---|---|---|
| Time | Product | pH 3 | pH 4 | pH 5 | pH 10 |
| 0 h | Example 1 | 39 | 39 | 41 | 27 |
|  | Comp. Ex. 9 | 34 | 28 | 29 | 27 |
| 1 day | Example 1 | 37 | 38 | 37 | 35 |
|  | Comp. Ex. 9 | 12 | 32 | 25 | 25 |
| 2 day | Example 1 | 39 | 39 | 36 | 38 |
|  | Comp. Ex. 9 | 10 | 41 | 25 | 33 |
| 7 days | Example 1 | 38 | 39 | 40 | 36 |
|  | Comp. Ex. 9 | 6 | 17 | 28 | 25 |

TABLE 7-continued

Effect of pH on Spreading Properties
Vs Time of Comparative Example 7.

| | | Spread Diameter (mm) | | | |
|---|---|---|---|---|---|
| Time | Product | pH 3 | pH 4 | pH 5 | pH 10 |
| 14 days | Example 1 | 39 | 37 | 39 | 39 |
| | Comp. Ex. 9 | 7 | 7 | 37 | 15 |
| 180 days | Example 1 | 43 | 40 | 44 | 41 |
| 365 days | Example 1 | 45 | 38 | 42 | 41 |

Examples 13-17

Effect of Co-surfactants on Blend Spreading Properties of Example 1

The impact of other ingredients on spreading was determined by blending the silylated polyether compound of the present invention, with a conventional organic based co-surfactant. The co-surfactants are displayed in Table 8.

Blends were prepared as physical mixtures where the weight fraction silicone is represented by α (alpha), indicating that the co-surfactant makes up the balance of the blend ratio. For example when α=0 this indicates that the composition contains 0% of the silylated polyether component and 100% co-surfactant, while an α=1.0 indicates the composition contains 100% silylated polyether component and no (0%) co-surfactant. Mixtures of the two components are represented by the weight fraction α, where α ranges as follows: 0≦α≦1.0. By example when α=0.25 this indicates the surfactant mixture is composed of 25% silylated polyether component and 75% co-surfactant. These blends are then diluted in water to the desired concentration for spreading evaluation.

Spreading was determined as described in accordance of the procedure above, at 0.1 weight percent total surfactant. The results are presented in Table 9.

TABLE 8

Description of Conventional Co-surfactants

| ID | Description |
|---|---|
| PAO-20 | Polyoxyethylene/polyoxypropylene copolymer (20% EO) |
| IDA-6 | Isodecyl alcohol ethoxylate (5-6 EO) |
| Oxo-TDA-5 | Oxo-tridecyl alcohol ethoxylate (5 EO) |
| APG | $C_{8-10}$ Alkylpolyglucoside |

Table 9 demonstrates that representative examples of the co-surfactants of the present invention provide favorable spreading results, and in some cases provide an unexpected synergistic enhancement, where the spread diameter of the mixture exceeds that of the individual components.

TABLE 9

Effect of Co-surfactants on Blend
Spreading Properties of Example 1

| Silylated | Wt Fraction (α) Silicone Surfactant Spread diameter (mm) | | | | | Co- |
|---|---|---|---|---|---|---|
| Ex. polyether | 0 | 0.25 | 0.50 | 0.75 | 1.0 | surfactant |
| 13 Example 1 | 6 | 21 | 32 | 40 | 44 | PAO-20 |
| 14 Example 1 | 8 | 20 | 35 | 40 | 44 | IDA-6 |
| 15 Example 1 | 24 | 41 | 43 | 45 | 44 | Oxo-TDA-5 |
| 16 Example 1 | 7 | 21 | 35 | 38 | 44 | APG |
| 17 Example 1 | na | 13 | 26 | 34 | 44 | None* |

*Silylated polyether compound 1 alone at relative concenrtion (i.e. alpha = 0.25 is 0.025% product from Example 1.

The following examples describe the utility and application of these novel surfactant compositions to provide improved flow, leveling and wetting benefits.

Example 18

A model waterborne modified acrylic lacquer formulation based on Rohm and Haas RHOPLEX® 1421 (pH 9.1), as presented in the Table 10, is prepared. The components are slowly mixed in the order they are listed in Table 10. Two drops of red dye are added to the formulation to allow greater contract of coating photographs. The coatings are applied by standard drawdowns onto opacity charts (manufactured by Leneta Company, Form 2A). The dry film thickness is ~1 mil. Visual evaluations are made one hour after application. The samples are rated using the visual aspect measurements on a scale of 0-5, 0 being coatings that are characterized with high occurrence of pin holing and complete lack of flow, leveling and wetting, 5 is characterized as defect free coatings.

TABLE 10

Waterborne Acrylic Coating Formulation

| Chemicals | Percentage, % |
|---|---|
| Silylated polyether 1 | 0.1-1.0 |
| 2-(2-Butoxyethoxy)ethanol | 10.00 |
| Water | 25.00-25.9 |
| RHOPLEX ® 1421 | 64.00 |
| Total | 100.00 |

Example 19

A model waterborne polyurethane dispersion (PUD) lacquer formulation based on Daotan® VTW 1236/40WANMP (manufactured by Cytec Surface Specialties Inc.), as shown in the Table 11 is prepared. The components are slowly mixed in the order they are listed in Table 11. Two drops of red dye are added to the formulation to allow greater contract of coating photographs. The coatings are applied by standard drawdown onto 4"x8" cold rolled steel (CRS) panels provided by ACT laboratories. Prior to use, the excess of machine oil is removed from the panels by wiping with delicate task wipes (manufactured by Kimwipes). The dry film thickness is ~1 mil. Visual evaluations are made one hour after application. The samples are rated using the visual aspect measurements on a scale of 0-5, 0 being coatings that are characterized with high occurrence of pin holing and complete lack of flow, leveling and wetting, 5 is characterized as defect free coatings.

TABLE 11

| PUD lacquer formulation | |
|---|---|
| Chemicals | Percentage, % |
| Silylated polyether 1 | 1.00 |
| Water | 25.00 |
| Daotan ® VTW 1236/40WANMP | 74.00 |
| Total | 100.00 |

A conventional printing ink formulation based on Joncryl 537 system (Johnson Polymer) is prepared to demonstrate the efficacy and advantages of the surfactants of the present invention and is presented in Table 12. Application of the coating is done using automatic film applicator, 25 microns rod at 25 to 30 DIN cup #4, and is allowed to air dry on 3 different substrates: Low-density polyethylene; High-density polyethylene; and Co-extruded polypropylene MB400 (Mobil), with formulations at pH 9.5. Visual evaluations are made one hour after application. The samples are rated using the visual aspect measurements on a scale of 0-5, 0 being coatings that are characterized with high occurrence of pin holing and complete lack of flow, leveling and wetting, 5 is characterized as defect free coatings. The Gloss of the coatings are measured with Byk Gardner glossmeter at 60°.

TABLE 14

| Printing Ink Formulation | | | |
|---|---|---|---|
| Name | Description | Supplier | Parts |
| Joncryl 537 | Acrylic Emulsion | Johnson Polymer | 60 |
| Dowanol DPnB | Coalascent | Dow | 6 |
| Jonwax 35 | Wax Dispersion | Johnson Polymer | 2 |
| Pigment paste | Pigment Blue (PB 15:4) dispersed in Joncryl 678 at 40% | Siegwerk | 5 |
| Surfactants: | Silylated polyether of Example 1 | | 0.5-2 |
| Rheolate 210 | Thickener | Elementis Specialties | 1 |
| Water | Water | Distilled Water | To adjust to 100 parts |

While the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the process of the invention but that the invention will include all embodiments falling within the scope of the appended claims.

The invention claimed is:

1. A coating composition comprising:
(a) at least one silylated polyether compound of the general formula (1):

$$(R^1)(R^2)(R^3)SiR^4Si(R^5)(R^6)R^7(C_2H_4O)_a(C_3H_6O)_b(C_4H_8O)_cR^8 \quad (1)$$

wherein
each $R^1$, $R^2$, $R^3$, $R^5$ and $R^6$ is methyl;
$R^4$ is methylene or ethylene;
$R^7$ is —$CH_2CH_2CH_2O$— or —$CH_2CH(CH_3)CH_2O$—;
$R^8$ is hydrogen or methyl; and
each occurrence of the subscripts a, b and c is an integer where a is 1 to 20, b is 0 to 4 and c is 0 to 4 with the provisos that (i) a is greater than or equal to 5 times (b+c) and (ii) the silylated polyether (a) is employed in the amount of 0.01 to 5 weight percent based upon the total weight of the composition; and
(b) at least one waterborne acrylic coating resin wherein the resin is an aqueous emulsion wherein the continuous phase comprises water and the discontinuous phase comprises polymer derived from at least one monomer selected from the group consisting of acrylonitrile, acrylic acid, methyl acrylate, ethyl acrylate, butyl acrylate, 2-ethylhexyl acrylate, methoxyethyl acrylate, diaminoethyl acrylate, methacrylic acid, methyl methacrylate, ethyl methacrylate, isobutyl methacrylate, 2-ethylhexyl methacrylate, lauryl methacrylate, stearic methacrylate, dimethylaminoethyl methacrylate, 2-hydroxylpropyl acrylate, 2-hydroxylpropyl methacrylate, acrylamide, methacrylamide and glycidyl acrylate and containing at least one reactive function group selected from carboxylate, epoxy, hydroxyl, amine, amide or vinyl and having a weight average molecular weight of from 50,000 grams per mole to 2,000,000 gram per mole, and a glass transition temperature of from −20° C. to 35° C.

2. The composition of claim 1 wherein the silylated polyether compound is selected from the group consisting of
$(CH_3)_3SiCH_2CH_2Si(CH_3)_2CH_2CH_2CH_2$—O—$(CH_2CH_2O)_7CH_3$,
$(CH_3)_3SiCH_2CH_2Si(CH_3)_2CH_2CH_2CH_2O(CH_2CH_2O)_{20}CH_3$, and
$(CH_3)_3SiCH_2CH_2Si(CH_3)_2CH_2CH(CH_3)CH_2O(CH_2CH_2O)_4CH_3$.

3. The composition of claim 1 wherein silylated polyether compound (a) employed is from 0.01 to 1 weight percent based upon the total weight of the composition.

4. The composition of claim 1 wherein the waterborne acrylic resin is polymer derived from at least one monomer selected from the group consisting of acrylic acid, methyl acrylate, ethyl acrylate, butyl acrylate, 2-ethylhexyl acrylate, methoxyethyl acrylate, diaminoethyl acrylate, methacrylic acid, methyl methacrylate, ethyl methacrylate, isobutyl methacrylate, 2-ethylhexyl methacrylate, lauryl methacrylate, stearic methacrylate, dimethylaminoethyl methacrylate, 2-hydroxylpropyl acrylate and 2-hydroxylpropyl methacrylate.

5. A coating composition comprising:
(a) at least one silylated polyether compound of the general formula (1):

$$(R^1)(R^2)(R^3)SiR^4Si(R^5)(R^6)R^7(C_2H_4O)_a(C_3H_6O)_b(C_4H_8O)_cR^8 \quad (1)$$

wherein $R^1$, $R^2$, $R^3$, $R^5$ and $R^6$ are methyl; $R^4$ is methylene, ethylene or propylene; $R^7$ is —$CH_2CH_2CH_2O$— or —$CH_2CH(CH_3)CH_2O$—; $R^8$ is hydrogen, methyl or acetyl; a is 2 to 10, b is 2 to 10; c is 0 to 10, with the provisos that (i) the ratio, a/(b+c) is from 0.1 to 5 and (ii) the silylated polyether (a) is employed in the amount of 0.01 to 5 weight percent based upon the total weight of the composition; and
(b) radiation-curable coating resin (b) selected from the group consisting of epoxy acrylates, polyester acrylates, acrylated epoxidized vegetable oils, fatty acid modified acrylates and epoxides which cures upon exposure to ultra-violet or electron beam radiation; and
(c) a reactive diluent selected from the group consisting of dipropyleneglycol diacrylate, tripropyleneglycol diacrylate, 1,6-hexanediol diacrylate, ethoxylated bisphenol-A diacrylate, pentaerythritol triacrylate, trimethylolpropanetriacrylate, propoxylated glycerol triacrylate, trimethylolpropane tetraacrylate, di-pentaerythritol pentaacrylate, and di-pentaerythritol hexaacrylate.

6. The composition of claim 5 wherein the silylated polyether compound (a) is selected from the group consisting of $(CH_3)_3SiCH_2CH_2Si(CH_3)_2CH_2CH_2CH_2O(CH_2CH_2O)_8$
$(CH_2CH(CH_3)O)_3CH_3$,
$(CH_3)_3SiCH_2CH_2Si(CH_3)_2CH_2CH_2CH_2O(CH_2CH_2O)_8$
$(CH_2CH(CH_3)O)_5CH_2CH(CH_2CH_3)OH$
$(CH_3)_3SiCH_2CH_2Si(CH_3)_2CH_2CH_2CH_2O(CH_2CH_2O)_4$
$(CH_2CH(CH_3)O)_8CH_3$, and mixtures thereof.

7. A coating composition comprising:
(a) at least one silylated polyether compound of the general formula (1):

$$(R^1)(R^2)(R^3)SiR^4Si(R^5)(R^6)R^7(C_2H_4O)_a(C_3H_6O)_b(C_4H_8O)_cR^8 \quad (1)$$

wherein $R^1$, $R^2$, $R^3$, $R^5$ and $R^6$ are methyl; $R^4$ methylene, ethylene or propylene; $R^7$ is —$CH_2CH_2CH_2O$— or —$CH_2CH(CH_3)CH_2O$—; $R^8$ is hydrogen, methyl or acetyl; a is from 15 to 40; b is 0 to 2; and c is 0, with the provisos that (i) the ratio, b/a is from 0 to 0.15 and (ii) the silylated polyether (a) is employed in the amount of 0.01 to 5 weight percent based upon the total weight of the composition; and
a thermosetting coating resin having a weight average molecular weight of from 1,000 grams per mole to 10,000 grams per mole selected from the group consisting of epoxy resin, unsaturated polyether resins and acrylic polymers.

8. The composition of claim 7 wherein the silylated polyether compound (a) is selected from the group consisting of
$(CH_3)_3SiCH_2CH_2Si(CH_3)_2CH_2CH_2CH_2O(CH_2CH_2O)_{15}CH_3$,
$(CH_3)_3SiCH_2CH_2Si(CH_3)_2CH_2CH_2CH_2O(CH_2CH_2O)_{30}CH_3$,
$(CH_3)_3SiCH_2CH_2Si(CH_3)_2CH_2CH_2CH_2O(CH_2CH_2O)_{40}CH_3$,
$(CH_3)_3SiCH_2CH_2Si(CH_3)_2CH_2CH_2CH_2O(CH_2CH_2O)_{18}H$,
$(CH_3)_3SiCH_2CH_2Si(CH_3)_2CH_2CH_2CH_2O(CH_2CH_2O)_{25}C(=O)CH_3$,
$CH_3)_3SiCH_2CH_2Si(CH_3)_2CH_2CH_2O(CH_2CH_2O)_{35}CH_2CH(CH_3)OH$, and mixtures thereof.

9. The coating composition of claim 1 further comprising at least one co-surfactant selected from the group consisting of alkoxylates, ethoxylates, block copolymers of ethylene oxide, copolymers of ethylene oxide, copolymers of propylene oxide, copolymers of butylene oxide, alkyl phenol ethoxylate, alkyl phenol propoxylate, arylarylalkoxylates, amine alkoxylates, amine ethoxylates; fatty acid alkoxylates, fatty alcohol alkoxylates, alkyl sulfonates, alkyl benzene sulfonates, alkyl naphthalene sulfonates, sulfated fatty alcohols, sulfated fatty alcohols, sulfated fatty amines, sulfated fatty acid amides, acid esters of sodium isethionate, esters of sodium sulfosuccinate, sulfated fatty acid esters, sulfonated fatty acid esters, petroleum sulfonates, N-acyl sarcosinates, alkyl polyglycosides, alkyl ethoxylated amines, alkyl acetylenic diols, pyrrilodone based surfactants, 2-ethyl hexyl sulfate, isodecyl alcohol ethoxylates, ethylene diamine alkoxylates, ethylene oxide/propylene oxide copolymers, diphenyl ether Gemini type surfactants, ethylene oxide/propylene oxide copolymers, amine ethoxylates, alkyl polyglycosides, and oxo-tridecyl alcohol ethoxylates.

10. A substrate coated with coating composition of claim 1.

11. A printing ink composition comprising:
(a) at least one silylated polyether compound of the general formula (1):

$$(R^1)(R^2)(R^3)SiR^4Si(R^5)(R^6)R^7(C_2H_4O)_a(C_3H_6O)_b(C_4H_8O)_cR^8 \quad (1)$$

wherein
each $R^1$, $R^2$, $R^3$, $R^5$ and $R^6$ is methyl;
$R^4$ is methylene or ethylene;
$R^7$ is —$CH_2CH_2CH_2O$— or —$CH_2CH(CH_3)CH_2O$—;
$R^8$ is hydrogen or methyl; and
each occurrence of the subscripts a, b and c is an integer where a is 1 to 20, b is 0 to 4 and c is 0 to 4 with the provisos that (i) a is greater than or equal to 5 times (b+c) and (ii) the silylated polyether (a) is employed in the amount of 0.01 to 5 weight percent based upon the total weight of the composition; and
(b) at least one printing ink resin wherein the printing ink resin is an aqueous emulsion wherein the continuous phase comprises water and the discontinuous phase comprises polymer derived from at least one monomer selected from the group consisting of acrylonitrile, acrylic acid, methyl acrylate, ethyl acrylate, butyl acrylate, 2-ethylhexyl acrylate, methoxyethyl acrylate, diaminoethyl acrylate, methacrylic acid, methyl methacrylate, ethyl methacrylate, isobutyl methacrylate, 2-ethylhexyl methacrylate, lauryl methacrylate, stearic methacrylate, dimethylaminoethyl methacrylate, 2-hydroxylpropyl acrylate, 2-hydroxylpropyl methacrylate, acrylamide, methacrylamide and glycidyl acrylate and containing at least one reactive function group, selected from carboxylate, epoxy, hydroxyl, amine, amide or vinyl and having a weight average molecular weight of from 50,000 grams per mole to 2,000,000 gram per mole and a glass transition temperature of from −20° C.

12. The composition of claim 11 wherein the silylated polyether compound (a) is selected from the group consisting of
$(CH_3)_3SiCH_2CH_2Si(CH_3)_2CH_2CH_2CH_2O(CH_2CH_2O)_7CH_3$,
$(CH_3)_3SiCH_2CH_2Si(CH_3)_2CH_2CH_2CH_2O(CH_2CH_2O)_{20}CH_3$, and
$(CH_3)_3SiCH_2CH_2Si(CH_3)_2CH_2CH(CH_3)CH_2O(CH_2CH_2O)_4CH_3$.

13. The composition of claim 11 wherein silylated polyether compound (a) employed is from 0.01 to 5 weight percent based upon the total weight of the composition.

14. The composition of claim 11 further comprising at least one co-surfactant selected from the group consisting of alkoxylates, ethoxylates, block copolymers of ethylene oxide, copolymers of ethylene oxide, copolymers of propylene oxide, copolymers of butylene oxide, alkyl phenol ethoxylate, alkyl phenol propoxylate, arylarylalkoxylates, amine alkoxylates, amine ethoxylates, fatty acid alkoxylates, fatty alcohol alkoxylates, alkyl sulfonates, alkyl benzene sulfonates, alkyl naphthalene sulfonates, sulfated fatty alcohols, sulfated fatty alcohols, sulfated fatty amines, sulfated fatty acid amides, acid esters of sodium isethionate, esters of sodium sulfosuccinate, sulfated fatty acid esters, sulfonated fatty acid esters, petroleum sulfonates, N-acyl sarcosinates, alkyl polyglycosides, alkyl ethoxylated amines, alkyl acetylenic diols, pyrrilodone based surfactants, 2-ethyl hexyl sulfate, isodecyl alcohol ethoxylates, ethylene diamine alkoxylates, ethylene oxide/propylene oxide copolymers, diphenyl ether Gemini type surfactants, ethylene oxide/propylene oxide copolymers, amine ethoxylates, alkyl polyglycosides, and oxo-tridecyl alcohol ethoxylates.

15. The composition of claim 11 exhibiting enhanced wetting, flow and leveling compared to identical composition absent said silylated polyether compound (a).

16. A substrate printed with an ink composition of claim 11.

* * * * *